US012751978B2

(12) United States Patent
Choy et al.

(10) Patent No.: US 12,751,978 B2
(45) Date of Patent: Oct. 6, 2026

(54) **TUMOR-TARGETING *SALMONELLA gallinarum* STRAIN AND USE THEREOF**

(71) Applicant: INDUSTRY FOUNDATION OF CHONNAM NATIONAL UNIVERSITY, Gwangju (KR)

(72) Inventors: Hyon El Choy, Gwangju (KR); Jae Ho Jeong, Gwangju (KR); Dae Jin Lim, Gwangju (KR); Hyung Ju Lim, Gwangju (KR); Kwangsoo Kim, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 1209 days.

(21) Appl. No.: 17/768,567

(22) PCT Filed: Oct. 29, 2020

(86) PCT No.: PCT/KR2020/014965
§ 371 (c)(1),
(2) Date: Apr. 13, 2022

(87) PCT Pub. No.: WO2021/086085
PCT Pub. Date: May 6, 2021

(65) Prior Publication Data
US 2024/0108664 A1 Apr. 4, 2024

(30) Foreign Application Priority Data
Oct. 31, 2019 (KR) ........................ 10-2019-0138224

(51) Int. Cl.

| | |
|---|---|
| ***A61K 35/74*** | (2015.01) |
| ***A61K 49/00*** | (2006.01) |
| ***A61P 35/00*** | (2006.01) |
| ***C12N 1/205*** | (2026.01) |
| ***C12N 1/36*** | (2006.01) |
| ***C12N 9/02*** | (2006.01) |
| ***C12N 9/12*** | (2006.01) |
| ***C12N 9/16*** | (2006.01) |
| ***C12N 15/74*** | (2006.01) |
| ***C12R 1/42*** | (2006.01) |

(52) U.S. Cl.
CPC .......... *A61K 35/74* (2013.01); *A61K 49/0097* (2013.01); *A61P 35/00* (2018.01); *C12N 1/205* (2021.05); *C12N 1/36* (2013.01); *C12N 9/0008* (2013.01); *C12N 9/1235* (2013.01); *C12N 9/16* (2013.01); *C12N 15/74* (2013.01); *C12Y 102/0105* (2013.01); *C12Y 207/06005* (2013.01); *C12Y 301/07002* (2013.01); *C12R 2001/42* (2021.05)

(58) Field of Classification Search
CPC ........ A61K 35/00; A61K 35/74; A61K 49/00; A61K 49/0097; A61P 35/00; C12N 1/205; C12N 1/36; C12N 9/0008; C12N 9/1235; C12N 9/16; C12N 15/74; C12N 15/52; C12N 9/1096; C12Y 102/0105; C12Y 207/06005; C12Y 301/07002; C12Y 206/01016; C12R 2001/42; Y02A 50/30; C12Q 1/02; G01N 21/763
See application file for complete search history.

(56) References Cited

U.S. PATENT DOCUMENTS

2012/0128594 A1 5/2012 Choy et al.

FOREIGN PATENT DOCUMENTS

| | | |
|---|---|---|
| KR | 10-2011-0095528 A | 8/2011 |
| KR | 10-2011-0126227 A | 11/2011 |
| KR | 10-2014-0107954 A | 9/2014 |
| KR | 10-1548734 B1 | 9/2015 |
| KR | 10-2016-0039495 A | 4/2016 |

OTHER PUBLICATIONS

Park et al, The Journal of Microbiology, vol. 48, No. 5, pp. 674-681 (Year: 2010).*
Lim et al, Molecular Therapy: Oncolytics, vol. 31, pp. 1-9 (Year: 2023).*
Jeong et al, Journal of Bacteriology, vol. 190, No. 19, pp. 6340-6350 (Year: 2008).*
Hernandez-Luna (Infection by *Salmonella enterica* promotes or demotes tumor development, pp. 1-17 (Year: 2018).*
International Search Report and Written Opinion mailed Feb. 15, 2021, for PCT International Application No. PCT/KR2020/014965, Choy et al., “Tumor-Targeting *Salmonella gallinarum* Strain and Use Thereof,” filed Oct. 29, 2020 (English translation) (16 pages).
Jeong et al., “*Salmonella enterica* serovar gallinarum requires ppGpp for internalization and survival in animal cells,” J. Bacteriol. 190(19):6340-6350 (2008).
Kim et al., “A novel balanced-lethal host-vector system based on glmS,” PLoS One 8(3):e60511 (2013) (11 pages).
Park et al., “Immune response induced by ppGpp-defective *Salmonella enterica* serovar Gallinarum in chickens,” J. Microbiol. 48(5):674-681 (2010).
Extended European Search Report dated Dec. 9, 2022 for European Patent Application No. 20882295.7, Choy et al., “Tumor-Targeting *Salmonella gallinarum* Strain and Use Thereof,” filed Oct. 29, 2020 (10 pages).

(Continued)

*Primary Examiner* — D. L. Jones
(74) *Attorney, Agent, or Firm* — Clark & Elbing LLP

(57) ABSTRACT

The present invention relates to a tumor-targeting *Salmonella gallinarum* strain and the use thereof. The tumor-targeting *Salmonella gallinarum* strain has excellent tumor proliferation inhibitory activity and enables tumor-specific targeting, and thus can be utilized for treatment and imaging of tumors without any side effects.

4 Claims, 9 Drawing Sheets
Specification includes a Sequence Listing.

(56) References Cited

OTHER PUBLICATIONS

Kaiser et al., "Differential cytokine expression in avian cells in response to invasion by *Salmonella typhimurium, Salmonella enteritidis* and *Salmonella gallinarum*," Microbiology (Reading). 146(12):3217-26 (2000).
Laniewski et al., "Evaluation of protective efficacy of live attenuated *Salmonella enterica* serovar Gallinarum vaccine strains against fowl typhoid in chickens," Clin. Vaccine Immunol. 21(9):1267-76 (2014).
Toley et al., "Motility is critical for effective distribution and accumulation of bacteria in tumor tissue," Integr Biol (Camb). 4(2):165-76 (Epub Dec. 2011) (Feb. 2012).

* cited by examiner

SEQUENCE LISTING

```
<160> NUMBER OF SEQ ID NOS: 8

<210> SEQ ID NO 1
<211> LENGTH: 70
<212> TYPE: DNA
<213> ORGANISM: Artificial Sequence
<220> FEATURE:
<223> OTHER INFORMATION: Synthetic Construct
```

<400> SEQUENCE: 1
gtggatcgca agcctgggaa tttccagcca gcagtcgtgt gagcgcttag gtgtaggctg 60
gagctgcttc 70

<210> SEQ ID NO 2
<211> LENGTH: 70
<212> TYPE: DNA
<213> ORGANISM: Artificial Sequence
<220> FEATURE:
<223> OTHER INFORMATION: Synthetic Construct

<400> SEQUENCE: 2
gtgcagtcgc cgtgcatcaa tcacatccgg cacctggttc agcttaccga attccgggga 60
tccgtcgacc 70

<210> SEQ ID NO 3
<211> LENGTH: 69
<212> TYPE: DNA
<213> ORGANISM: Artificial Sequence
<220> FEATURE:
<223> OTHER INFORMATION: Synthetic Construct

<400> SEQUENCE: 3
ttaagcgtct tcggcaggcg tatctcgttg cacgtgacgc tcacgagggc tgtaggctgg 60
agctgcttc 69

<210> SEQ ID NO 4
<211> LENGTH: 70
<212> TYPE: DNA
<213> ORGANISM: Artificial Sequence
<220> FEATURE:
<223> OTHER INFORMATION: Synthetic Construct

<400> SEQUENCE: 4
gccagatgta cgcgatcgcg tgcggtaagg cgaataaagg tactatagac catatgaata 60
tcctccttag 70

<210> SEQ ID NO 5
<211> LENGTH: 83
<212> TYPE: DNA
<213> ORGANISM: Artificial Sequence
<220> FEATURE:
<223> OTHER INFORMATION: Synthetic Construct

<400> SEQUENCE: 5
ttactcaacc gtaaccgatt ttgccaggtt acgcggctgg tcaacgtcgg tgccttgatt 60
gtgtaggctg gagctgcttc gaa 83

<210> SEQ ID NO 6
<211> LENGTH: 83
<212> TYPE: DNA
<213> ORGANISM: Artificial Sequence
<220> FEATURE:
<223> OTHER INFORMATION: Synthetic Construct

<400> SEQUENCE: 6
atgtgtggaa ttgttggcgc gatcgcgctt cgtgatgtag ctgaatcctt cttgaaggtc 60
atatgaatat cctccttcgt tcc 83

<210> SEQ ID NO 7
<211> LENGTH: 26

-continued

```
<212> TYPE: DNA
<213> ORGANISM: Artificial Sequence
<220> FEATURE:
<223> OTHER INFORMATION: Synthetic Construct

<400> SEQUENCE: 7

aagtcgacat gtgtggaatt gttggc                                          26


<210> SEQ ID NO 8
<211> LENGTH: 30
<212> TYPE: DNA
<213> ORGANISM: Artificial Sequence
<220> FEATURE:
<223> OTHER INFORMATION: Synthetic Construct

<400> SEQUENCE: 8

gggtcgactt actctacggt aaccgatttc                                      30
```

TUMOR-TARGETING *SALMONELLA gallinarum* STRAIN AND USE THEREOF

SEQUENCE LISTING

The instant application contains a Sequence Listing which has been submitted electronically in ASCII format and is hereby incorporated by reference in its entirety. Said ASCII copy, created on Mar. 8, 2022, is named 50413-229001_Sequence_Listing_3_8_22_ST25 and is 2,333 bytes in size.

TECHNICAL FIELD

The present disclosure relates to a tumor-targeting *Salmonella gallinarum* strain and a use thereof.

BACKGROUND ART

Cancer is one of the most common causes of death, and recently, the incidence of cancer is on the rise due to environmental factors including environmental pollutants such as air pollution, and personal factors including high-fat intake due to westernization of diet, drinking alcohol, and smoking increase. Therefore, the development of anticancer materials for early prevention and treatment of cancer is becoming important. Compound-based anticancer drugs act on cancerous cells, but often exhibit non-specificity affecting the whole body, with the problem of adverse effects.

Since bacterial suppression of cancer has been reported, studies have been conducted into strains exhibiting anticancer effects. In the last 20 years, studied have been focused on the use of viable bacteria for cancer therapy, finding diverse variants of *Bifidobacterium, Clostridium, Lactococcus, Shigella, Vibrio, Listeria, Escherichia*, and *Salmonella* spp. in cancer animal models. However, the basic mechanism of cancer treatment using such strains is not fully understood yet.

Among them, *Salmonella* spp. have been studied for use as an anticancer target carrier and use for inhibiting cancer growth (patent document 1). However, the *Salmonella* strains studied previously exhibit low cancer cell targeting rates because of their distribution in various organs as well as cancerous cells. In addition, adverse effects are caused by the strains themselves. Particularly in patients or the elderly with weakened immune function, even the *Salmonella* strain of lowered pathogenicity may cause fatal sepsis. In addition, the conventional *Salmonella* strains have difficulty in achieving effective therapy and delivering anticancer substance into cells due to their low viability in cancer tissues.

With respect to *Salmonella gallinarum* strains, a vaccine composition and a feed composition for prevention of fowl typhoid are disclosed (patent document 2), but nowhere is the cancer treatment efficacy of the strains described.

Leading to the present disclosure, intensive and thorough research conducted by the present inventors resulted in the finding that an attenuated *Salmonella gallinarum* strain deficient in guanosine tetraphosphate (ppGpp) synthesis exhibits superiority in targeting and viability for cancer cells, but inferiority in targeting and viability for normal organs, compared to conventional *Salmonella typhimurium* strains and as such, can be effectively used for cancer therapy.

RELATED ART DOCUMENT

Patent Literature (Patent Literature 1) Korean Patent No. 10-2015573

(Patent Literature 2) Korean Patent No. 10-2011-0126227 A

DISCLOSURE OF INVENTION

Technical Problem

An aspect of the present disclosure is to provide an attenuated *Salmonella gallinarum* strain lacking guanosine tretraphosphate (ppGpp) production capability.

Another aspect of the present disclosure is to provide a pharmaceutical composition comprising the *Salmonella gallinarum* strain for prevention or treatment of tumor.

A further aspect of the present disclosure is to provide a method for providing information about tumor analysis, the method comprising the steps of: administering the *Salmonella gallinarum* strain to a subject; detecting bioluminescence of the strain; and determining the presence of tumor in the subject if the bioluminescence is detected.

In the present disclosure, the subject may be animals including or except for humans.

Solution to Problem

The present inventors have conducted research into the development of a *Salmonella* strain with targeting and viability excellent for cancer cells, but poor for normal organs, which leads to the present disclosure.

An aspect of the present disclosure provides an attenuated *Salmonella gallinarum* strain lacking guanosine tetraphosphate (ppGpp) production capability.

Being able to specifically target tumors, the attenuated *Salmonella gallinarum* lacking ppGpp production capability according to the present disclosure allows for effective therapy for tumors with minimal damages on normal organs except for tumorous tissues and thus can find advantageous applications in preventing, alleviating, or treating tumors.

As used herein, the term "attenuated" refers to modified to lower pathogenicity of a strain. Attenuation makes it possible to prevent the pathogenicity of the strain from causing cytotoxicity and other adverse effects in normal cells other than tumor cells. Attenuated strains can be constructed using various methods known in the art. By way of example, the attenuation is made by deletion or destruction of a virulence factor so that the strain can be viable in host cells. In this regard, pab, proBC, nadA, pncB, pmi, rpsL, ompR, htrA, hemA, rfc, poxA, gal U, aro, galE, cya, cyp, crp, cdt, pur, phoP, phoQ, ssa, guaA, guaB, clpP, clpX fliD, flgK, flgL, relA, spoA, and spoT genes, and the genes, encoded by *Salmonella* Pathogenicity Islands, including ssaV, sseBCD, ssrAB, sopB, sseF, and sseG, can be deleted to achieve the attenuation.

According to an embodiment of the present disclosure, the strain is a variant of the *Salmonella gallinarum* SG4021 strain (microorganism accession number: KCTC13985BP) as a result of deleting guanosine tetraphosphate production capability therefrom.

The *Salmonella gallinarum* SG4021 strain is a clinical isolate from the livers of chickens with fowl typhoid, reared in a Korean chicken farm and was deposited with the Korean Research Institute of Bioscience and Biotechnology (microorganism accession number: KCTC13985BP) on Oct. 8, 2019.

According to an embodiment of the present disclosure, the strain may be *Salmonella gallinarum* SG4023 (microorganism accession number: KCTC14338BP).

According to an embodiment of the present disclosure, the strain may lack a gene coding for ppGpp synthetase and may be attenuated as a result of deleting a gene coding for ppGpp synthetase.

The term "ppGpp", as used herein, refers to guanosine tetraphosphate and may be interchangeably used with guanosine 5'-diphosphate 3'-diphosphate or guanosine 3',5'-bispyrophosphate.

According to an embodiment of the present disclosure, the gene may include relA and spoT.

ppGpp, which is an intracellular signal transduction messenger, functions to induce the expression of genes encoded by *Salmonella* pathogenicity island (SPI) among the genes responsible for the toxicity of *Salmonella gallinarum* strains, and is encoded by relA and spoT genes. Therefore, *Salmonella gallinarum* strain lacking relA and spoT genes may become weaker in pathogenicity by one million fold or greater than the wild-type *Salmonella*, so that effective attenuation is possible.

The ppGpp-deficient variant according to the present disclosure may be produced by deleting both the relA and spoT genes.

The deletion of both relA and spoT genes may be made by modification of relA and spoT genes to bring about impairment into the transcription or translation of the genes or the activity of the gene products. Such genetic modifications may include inactivation of not only an ppGpp synthetase coding sequence, but also a promoter thereof. Specific inactivation of only a target gene on the genome of *Salmonella gallinarum* may be achieved by a mutation through substitution, insertion, deletion, or a combination thereof on the entire area or one partial area of the coding gene. For example, the deletion of a gene or the insertion of a heterogenous sequence into a gene may result in gene truncation, a nonsense mutation, a frameshift mutation, a missense mutation, and so on. Such specific gene inactivation can be carried out using a method usually used in the art. The deletion of a gene may be conducted using various mutagenesis methods known in the art. For example, the deletion of relA and spoT genes may be achieved by PCR mutagenesis and cassette mutagenesis.

According to an embodiment of the present disclosure, the strain may lack a glmS gene.

According to an embodiment of the present disclosure, the strain may be *Salmonella gallinarum* SG4031 (microorganism accession number: KCTC14339BP).

The glmS gene-deficient *Salmonella gallinarum* can be lysed in the animal system due to the lack of the peptidoglycan constituent D-glucosamine (GlcN) or N-acetyl-D-glucosamine (GlcNAc). Thus, the gene can be used as a selective determinant for the strain.

With respect to the method of deleting a glmS gene, the contents overlapping with the above description are omitted to avoid undue complexity of the specification.

According to an embodiment of the present disclosure, the strain may be a transformant anchoring a plasmid carrying a glmS gene operatively linked to a promoter. In detail, the strain may have a glmS-deleted mutation on the chromosome thereof.

According to an embodiment of the present disclosure, a balanced-lethal host-vector system may be constructed by transformation of a plasmid carrying a glmS gene for compensating for a glmS deleted mutation on the chromosome thereof. The attenuated *Salmonella gallinarum* strain into which a plasmid carrying a glmS gene has been successfully transformed can synthesize GlcN or GlcNAc and survive even a GlcN- or GlcNAc-insufficient environment. Thus, the attenuated strain can serve as a selection marker.

The term "operatively linked", as used herein, refers to functional linkage between a gene expression control sequence and a different nucleotide sequence. The gene expression control sequence may be at least one selected from the group consisting of a replication origin, a promoter, and a transcription terminator. The transcription terminator may be a polyadenylation sequence (pA) and examples of the replication origin include f1 replication origin, SV40 replication origin, pMB1 replication origin, adeno replication origin, AAV replication origin, and BBV replication origin, but are not limited thereto.

As used herein, the term "promoter" refers to a region of DNA, located upstream of a structural gene, to which an RNA polymerase binds to initiate transcription.

A promoter according to an embodiment of the present disclosure may be a polynucleotide fragment about 100 bp to about 2500 bp long, functioning as a transcriptional regulatory sequence for regulating the transcription initiation of a specific gene. For example, the promoter may be selected from the group consisting of tac promoter, lac promoter, lacUV5 promoter, lpp promoter, pLλ promoter, pRλ promoter, rac5 promoter, amp promoter, recA promoter, SP6 promoter, trp promoter, T7 promoter, pBAD promoter, Tet promoter, trc promoter, pepT promoter, sulA promoter, pol 11(dinA) promoter, ruv promoter, uvrA promoter, uvrB promoter, uvrD promoter, umuDC promoter, lexA promoter, cea promoter, caa promoter, recN promoter, pagC promoter, and a synthetic promoter, but with no limitations thereto.

A plasmid according to an embodiment of the present disclosure may be any one used in the art and may be, for example, selected from the group consisting of pcDNA seriese, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19, but with no limitations thereto.

The plasmid of the present disclosure may include at least one selective marker. The marker is a nucleic acid sequence characterized by ability to be selected by a chemical method and may be accounted for by a gene that allows the discrimination of transformed cells from non-transformed cells. For example, the marker may be a gene resistant to a herbicide, such as glyphosate, glufosinate ammonium, or phosphinothricin; or a gene resistant to an antibiotic such as ampicillin, kanamycin, G418, bleomycin, hygromycin, or chloramphenicol, but with no limitations thereto.

The plasmid of the present disclosure may be constructed using a genetic recombination technique known in the art, and site-specific DNA cleavage and ligation may be carried out using enzymes generally known in the art.

The plasmid of the present disclosure may be transformed into the *Salmonella gallinarum* strain by a method that is typically used in the art to introduce a nucleic acid into cells. The transformation may be carried out a suitable standard technique known in the art. For example, the transformation method may be electroporation, calcium phosphate ($CaPO_4$) precipitation, calcium chloride ($CaCl_2$) precipitation, microinjection, and use of polyethylene glycol (PEG), DEAE-dextran, cationic liposome, and lithium acetate-DMSO, but with no limitations thereto.

According to an embodiment of the present disclosure, the plasmid may further include a luminescence gene.

As used herein, the term "luminescence gene" refers to a gene encoding a protein that allows for luminescence imaging in vivo or ex vivo (in vitro) and is intended to encompass bioluminescence genes (e.g., luciferase gene), chemiluminescence genes, and fluorescence genes of various origins. An imaging device for the luminescence phenomenon expressed by such genes is known in the art and may be appropriately selected by a person skilled in the art.

Targeting tumors, the *Salmonella gallinarum* strain transformed with a plasmid including a luminescence gene according to an embodiment of the present disclosure allows tumors to be visibly monitored and as such, can increase the accuracy and effect of tumor therapy. An imaging device that can be used in association with the luminescence gene of the present disclosure may be appropriately selected by a person skilled in the art.

According to an embodiment of the present disclosure, the luminescence gene may be luxCDABE.

Herein, "luxCDABE" is a DNA fragment including all a gene coding for luciferase (heterodimer of luxA and luxB) and genes (luxC, luxD, and luxE) coding for tetradecanal, which is a luciferase substrate. The light-emitting compound luciferin is activated by ATP in cells and the active luciferin undergoes a luciferase-catalyzed reaction with oxygen with the concomitant emission of light through conversion from chemical energy to light energy.

Another aspect of the present disclosure provides a pharmaceutical composition comprising the *Salmonella gallinarum* strain for prevention or treatment of tumors.

The pharmaceutical composition of the present disclosure may include a pharmaceutically acceptable carrier. So long as it is typically used for preparing medications, any pharmaceutically acceptable carrier may be included in the pharmaceutical composition of the present disclosure. Examples of the pharmaceutically acceptable carrier include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, but are not limited thereto. In addition to the ingredients, the pharmaceutical composition of the present disclosure may further include a lubricant, a humectant, a sweetener, an emulsifier, a suspending agent, a preservative, and so on. For details of suitable pharmaceutically acceptable carriers and compositions, reference may be made to *Remington: the science and practice of pharmacy* 22nd edition (2013).

The pharmaceutical composition of the present disclosure may include various bases and/or additives necessary and suitable for formulations and can be formulated together with a non-ionic surfactant, a silicon polymer, a extender pigment, an aromatic, a preservative, a sterilizer, an oxidation stabilizer, an organic solvent, an ionic or non-ionic thickener, a softener, an antioxidant, a free radical scavenger, an opacifier, an emollient, silicone, α-hydroxy acid, a foaming agent, a moisturizer, a vitamin, an insect repellent, a flavorant, a preservative, a surfactant, an anti-inflammatory agent, a substance P antagonist, a filler, a polymer, a propellant, an alkalifying or acidifying agent, or a colorant within such an amount range as not to degrade the effect thereof.

A suitable dose of the pharmaceutical composition of the present disclosure may be prescribed depending on various factors including formulation methods, administration modes, the patient's age, body weight, sex, illness condition, and diet, the time of administration, the route of administration, excretion rates, and responsiveness. The pharmaceutical composition of the present disclosure may be administered at a dose of 0.001 to 1000 mg/kg to an adult. Meanwhile, the dosage unit may range from, for example, about $10^4$ to $10^{10}$ CFU, but with no limitations thereto. It may be administered once or in divided forms a day and a daily dosage may be $10^4$ to $10^{10}$ CFU, but with no limitations thereto.

The pharmaceutical composition of the present disclosure may be parenterally administered.

The pharmaceutical composition of the present disclosure may be parenterally administered and preferably intravenously, but with no limitations thereto.

For a formulation in a parenteral dosage form, for example, the pharmaceutical composition of the present disclosure may be mixed with a stabilizer or buffer in water to give a solution or suspension which is then prepared into ampule or vial dosage units. In addition, the composition may further include an auxiliary additive such as a stabilizer, a wettable powder or an emulsificant, a salt for adjustment of an osmotic pressure, and a buffer, and other therapeutically effective materials and may be formulated using a typical method.

According to an embodiment of the present disclosure, the tumor may be a solid tumor.

According to an embodiment of the present disclosure, the tumor may be adenocarcinoma.

According to an embodiment of the present disclosure, the tumor may be selected from the group consisting of colorectal cancer, pancreatic cancer, skin cancer, and breast cancer.

Adenocarcinoma is a type of cancerous tumor that occurs in cells of glands, including mucous membranes such as in stomach, intestine, bronchus, uterine, gall bladder, etc., glandular tissues or excretory ducts such as in prostate, thyroid gland, and pancreas.

According to previous studies on anticancer targeting therapy using bacteria, it is reported that immune responses and cytokine delivery in tumor cells can induce an anticancer immune effect without the adverse effect of systemic toxicity (Saltzman D A, Heise C P, Hasz D E, et al Attenuated *Salmonella typhimurium* containing interleukin-2 decreases MC-38 hepatic metastases: A novel anti-tumor agent Cancer Biother Radio 1996; 11:145-53; Sorenson B S, Banton K L, Frykman N L, Leonard A S, Saltzman D A Attenuated *Salmonella typhimurium* with IL-2 gene reduces pulmonary metastases in murine osteosarcoma Clin Orthop Relat R 2008; 466:1285-91) and that the growth of cancer cells is inhibited by inducing the deposition of leucocytes and neutrophils around tumors (Loeffler M, Le'Negrate G, Krajewska M, Reed J C Attenuated *Salmonella* engineered to produce human cytokine LIGHT inhibit tumor growth Proceedings of the National Academy of Sciences of the United States of America 2007; 104:12879-83; Loeffler M, Le'Negrate G, Krajewska M, Reed J C *Salmonella typhimurium* engineered to produce CCL21 inhibit tumor growth Cancer Immunol Immun 2009; 58:769-75).

In the present disclosure, the targeting activity of *Salmonella gallinarum* for colorectal cancer, pancreatic cancer, skin cancer, and breast cancer cell lines was found, together with the confirmation of the excellent anticancer effect of ΔppGpp *Salmonella gallinarum* strain according to an embodiment of the present disclosure in a mouse model of CT26 tumor, which is a type of adenocarcinoma. In this context, thus, the *Salmonella gallinarum* strain according to an embodiment of the present disclosure can exhibit various inhibitory activities against adenocarcinoma by targeting various adenocarcinomas such as colorectal cancer, pancreatic cancer, skin cancer, and breast cancer, and inducing the expression of cytokines and/or the deposition of leukocytes.

A further aspect of the present disclosure provides a method for providing information about tumor analysis, the method comprising the steps of: administering the *Salmonella gallinarum* strain to a subject; detecting bioluminescence of the strain; and determining the presence of tumor in the subject if the bioluminescence is detected.

With respect to the method of injecting the *Salmonella gallinarum* strains to a subject and the method of detecting bioluminescence, the contents overlapping with the above description are omitted to avoid undue complexity of the specification.

The tumor cells targeted by the *Salmonella gallinarum* strain transformed with a luminescence gene according to an embodiment of the present disclosure can be detected due to the luminescence gene whereby information about the presence or absence of tumor in the subject and the position, size, and temporal change pattern of the tumor present in the subject can be acquired.

Advantageous Effects of Invention

According to the tumor targeting *Salmonella gallinarum* strain and the use thereof, the strain has excellent inhibitory activity against tumor growth and can specifically target tumors, thus finding advantageous applications in tumor therapy and imaging without adverse effects.

BEST MODE FOR CARRYING OUT THE INVENTION

Figure 1A:
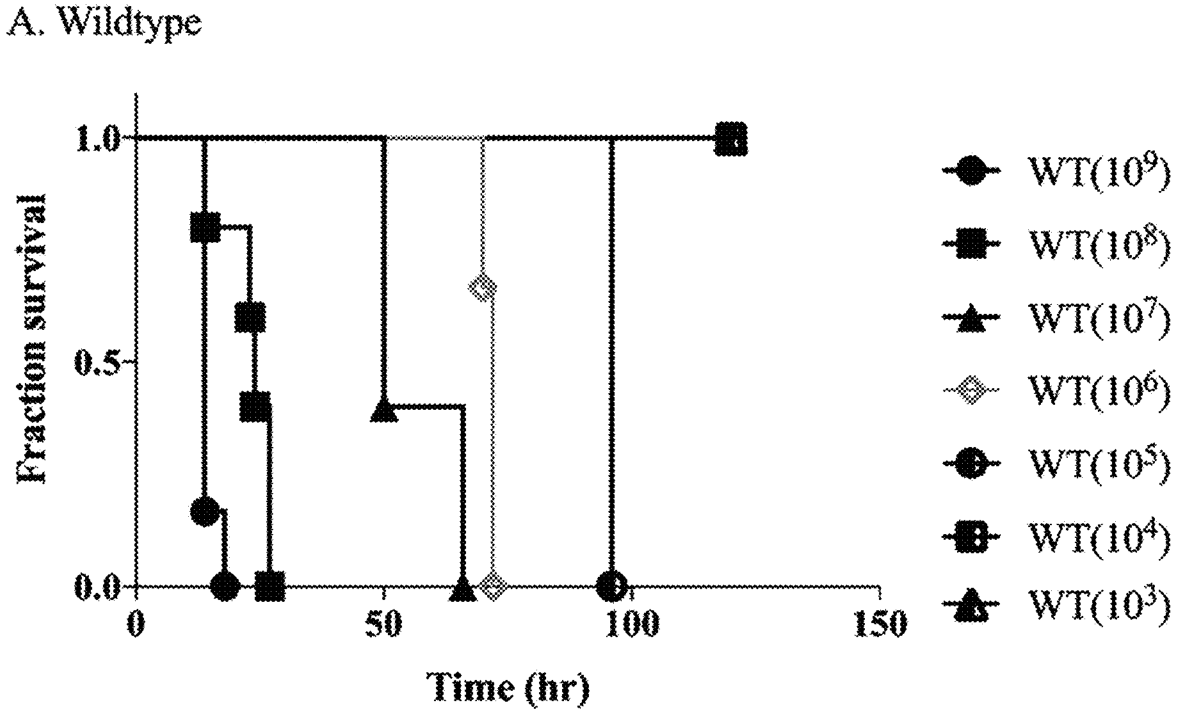
FIG. 1 shows plots of survival rates of BALB/c mice according to doses of (A) the wild-type *Salmonella gallinarum* strain (SG4021) or (B) the ppGpp-deleted *Salmonella gallinarum* (SG4023) after intravenous injection.

A better understanding of the present disclosure will be obtained from the following Examples which are set forth to illustrate the present disclosure and are not to be construed as limiting the present disclosure.

Example 1. Preparation of Attenuated *Salmonella gallinarum* Strain and Assay for Tumor Inhibition Activity

1-1. *Salmonella* Strain Growth

*Salmonella* spp. were grown at 37° C. in LB medium containing 1% NaCl (Difco Laboratories) under vigorous aeration. A solid support medium was prepared with 1.5% granule agar (Difco Laboratories). Antibiotics were purchased from Sigma Chemical. If necessary, the antibiotics ampicillin, kanamycin, and chloramphenicol were added at respective concentrations of 50 μg/ml, 50 μg/ml, and 15 μg/ml and N-acetyl-D-glucosamine (GlcNAc) was added at a concentration of 100 mg/ml. The bacteria in the broth were roughly estimated using a hemocytometer.

1-2. *Salmonella* Strain Lineage

Serotype *gallinarum* variants were originated from the clinical isolate SG 4021 from the livers of chickens with fowl typhoid, bred in a Korean farm (Table 1), and the SG4021 strain was deposited with the Korean Research Institute of Bioscience and Biotechnology (microorganism accession number: KCTC13985BP) on Oct. 8, 2019.

TABLE 1

| Strain | Lineage | Description |
|---|---|---|
| *S. gallinarum* | SG4021 | wild-type clinical isolate |
| | SG4022 | relA::kan, spoT::cat |
| | SG4023 | ΔrelA, ΔspoT |
| | SG4030 | ΔrelA, ΔspoT, glmS::kan |
| | SG4031 | ΔrelA, Δspot, ΔglmS |
| | SG4032 | ΔrelA, ΔspoT/GlmS$^+$pLux |
| | SG4033 | ΔrelA, ΔspoT, ΔglmS/ GlmS$^+$pLux |
| *S. typhimurium* | SHJ2037 | relA::kan, spoT::cat |
| | SMR2130 | ΔrelA, Δspor |

All the *Salmonella* strain lineages were constructed according to the method developed by Datsenko and Wanner (Proceedings of the National Academy of Sciences 97.12 (2000): 6640-6645), and the attenuation of *Salmonella* strains was induced by ppGpp deletion (ΔppGpp). The ppGpp deleted mutation was made by sequentially introducing relA::kan and spoT::cat into the genome of SG4021. In the glmS open reading frame, the gene carrying kan or cat was produced by PCR amplification using a pair of 60-nt primers, each including a 40-nt homology extension and a 20-nt priming sequence, with pKD13 serving as a template (Table 2).

TABLE 2

| Primer | | Primer base sequence (5'-3') | SEQ ID NO: |
|---|---|---|---|
| relA::kan | forward | GTCGTGTGAGCGCTTAGGTGTAGGCTGGAGCTGGTGGATCGCAAGCCTGGGAATTTCCAGCCAGCACTTC | SEQ ID NO: 1 |
| | reverse | CTGGTTCAGCTTACCGAATTCCGGGGATCCGTCGTGCAGTCGCCGTGCATCAATCACATCCGGCACGACC | SEQ ID NO: 2 |
| spoT::cat | forward | GTGACGCTCACGAGGGCTGTAGGCTGGAGCTGCTTAAGCGTCTTCGGCAGGCGTATCTCGTTGCACTTC | SEQ ID NO: 3 |
| | reverse | GCCAGATGTACGCGATCGCGTGCGGTAAGGCGAATAAAGGTACTATAGACCATATGAATATCCTCCTTAG | SEQ ID NO: 4 |
| glmS::kan | forward | CGGCTGGTCAACGTCGGTGCCTTGATTGTGTAGTTACTCAACCGTAACCGATTTTGCCAGGTTACGGCTGGAGCTGCTTCGAA | SEQ ID NO: 5 |
| | reverse | GATGTAGCTGAATCCTTCTTGAAGGTCATATGAATGTGTGGAATTGTTGGCGCGATCGCGCTTCGTATATCCTCCTTCGTTCC | SEQ ID NO: 6 |

Then, the purified PCR amplicons were transformed by electroporation into a *Salmonella* strain containing a lambda Red helper plasmid (pKD46). The mutants were confirmed by PCR using original and general test primers. Before induction of SG4023 from SG4022, the antibiotic resistant gene was deleted using a helper plasmid carrying pCP20, which is a FLP recombinant enzyme.

In addition, glmS deleted mutants were produced by the method developed by Datsenko and Wanner (Proceedings of the National Academy of Sciences 97.12 (2000): 6640-6645) (Kaiser et al., Microbiology, 146 Pt 12: 3217-3226, 2000). *Salmonella* cells are prone to releasing a plasmid carrying a reporter gene unnecessary for survival particularly in animals, but it is difficult to employ an antibiotic resistant gene for a selection determinant. Thus, use was made of glmS deleted mutant phenotypes that are lysed in the animal system due to the insufficiency of the peptidoglycan constituent D-glucosamine (GlcN) or N-acetyl-Dglucosamine (GlcNAc) which is an essential nutrient for. The red recombinase system of bacteriophage lambda was used to inactivate the genomic glmS gene in the *Salmonella gallinarum* strain.

1-3. GlmS+pLux Plasmid

To assay tumor targeting capability through bioluminescence and compensate for glmS deleted mutation on the chromosome, the balanced-lethal host-vector system having the glmS gene of *Salmonella gallinarum* incorporated thereinto was constructed.

Briefly, pLux carrying the lux operon (luxCDABE, ca. 9.5 kb) of Photobacterium leiognathid was inserted into the XbaI restriction enzyme site of a pUC19 plasmid backbone. For use in constructing a plasmid carrying both a lux operon cassette and glmS, the glmS gene of *Salmonella gallinarum* was amplified using the primers of Table 3.

TABLE 3

| Primer | | Primer base sequence (5'-3') | SEQ ID NO: |
|---|---|---|---|
| glmS | forward | AAGTCGACATGTGTGGAATTGTTGGC | SEQ ID NO: 7 |
| | reverse | GGGTCGACTTACTCTACGGTAACCGATTTC | SEQ ID NO: 8 |

The amplified 1.8 kb fragment was digested with Sal I and ligated to the same site of a pLux vector to construct GlmS+pLux. The glmS deleted mutant *Salmonella* strain transformed with the GlmS+pLux plasmid construct survives even an environment in D-glucosamine (GlcN) and N-acetyl-Dglucosamine (GlcNAc) and exhibits bioluminescence to allow for analysis through optical bioluminescent imaging.

1-4. Tumor Cell Line

From the American Type Culture Collection, murine CT26 colon carcinoma cells, 4T1 breast carcinoma cells, B16F10 melanoma cells, and human ASPC1 pancreas adenocarcinoma cells were purchased. CT26 and 4T1 cells were grown in high-glucose DMEM (Dulbecco's modified Eagle's medium) supplemented with 10% fetal bovine serum (FBS) and 1% penicillin-streptomycin. Murine B16F10 melanoma cells and ASPC1 cells were grown in RPMI 1640 supplemented with 10% FBS and 1% penicillin-streptomycin.

1-5. Assay for Plasmid Stability

Passage (1/1000) was made overnight in a flesh LB medium which was supplemented every 12 hours. Samples were taken every 24 hours and diluted. A suitable volume was spread three times over GlcNAc-supplemented LB plates irrespective of the presence or absence of ampicillin. Using the number of colonies thus formed, fractions of *Salmonella* spp. having the plasmid in total viable cells (colony forming unit, CFU) were calculated.

1-6. Mouse Model Construction

The cultured, various tumorous cells were xeno-grafted into the right thigh of each mouse to construct mouse tumor models. From Samtako Company (Korea), male mice at 5 to 8 weeks of age, each weighing 20 to 30 g, were purchased.

Management, experiments, and euthanasia were performed on all the animals according to an approved protocol.

Mice with subcutaneous tumor were constructed as follows: the in vitro cultured tumor cells of Example 1-4 were harvested and suspended in 30 μl of PBS, followed by subcutaneous injection of $1\times10^6$ cells of each of CT26, 4T1, and B16F10, and $1\times10^7$ cells of ASPC1 into right thighs of the mice. For hetero-implantation of tumor cells, injection was made of CT26 and 4T1 cells into BALB/c mice, B16F10 cells into C57/BL6 mice, AsPC-1 cells into BALB/c athymic $nu^-/nu^-$ mice.

When the tumor size reached 0.5 cm 3 after implantation of tumor cells (about 14 days after implantation), the ppGpp-deleted *Salmonella gallinarum* strain with mutation glmS of Example 1-2 including $GlmS^+$pLux of Example 1-3 or *Salmonella typhimurium* were administered at a dose of about $1\times10^7$ or about $1\times10^8$ CFU/ml of PBS via tail vein (0 day, 0 dpi).

1-7. Assay for Distribution of *Salmonella* Spp. in Mouse Internal Organ

To evaluate the number of live *Salmonella* spp., ΔppGpp *Salmonella typhimurium* and ΔppGpp *Salmonella* 5 *gallinarum* strain were intravenously at ca. $1\times10^7$ CFU and at ca. $1\times10^8$ CFU, respectively, into mouse groups (n=5). Days 1, 5, 10, and 16 after injection, the mice were sacrificed. Organs were excised and homogenized by a homogenizer in sterile PBS containing 0.05% Tween-20. *Salmonella* spp. were recovered from the homogenate and plated onto agar plates containing 50 μg/ml kanamycin and 15 μg/ml chloramphenicol.

1-8. Analysis for Tumor Size and Mouse Survival Rate

Tumor volumes were calculated according to the following formula.

$$\text{Tumor volume (mm}^3\text{)}=(\text{tumor length}\times\text{tumor height}\times\text{tumor width})/2$$

All animal experiments were approved by the Chonnam National University Institutional Animal Care and Use Committee (NO. CNU IACUC-H-2016-15). According to the instruction, mice with a tumor volume of 1,500 $mm^3$ or larger were sacrificed, and the survival rates of mice were evaluated according to the Gehan-Breslow-Wilcoxon test.

1-9. Optical Bioluminescence Imaging

In order to image the bioluminescence of *Salmonella* spp. as an index for targeting tumors, mice were anesthetized with 2% isoflurane and then placed in a light-blocked chamber of CCD (charged couple detector) camera-installed IVIS100 (Caliper, Hopkinton, MA, USA). The photons emitted from luciferase-expressing *Salmonella* spp. were collected and integrated for 1 minute. Pseudo color images representing counted photons were overlaid on bright optical images of rats using living image software version v.2.25 (Xenogen-Caliper, Hopkinto, Mass.).

1-10. Immunofluorescent Staining and Confocal Microscopy

In order to stain *Salmonella* strains in tumors, the isolated tissues were fixed overnight at room temperature with 3.4% paraformaldehyde in PBS and embedded into Optimal Cutting Temperature compound (OCT; Tissue-Tek). Subsequently, the tissues were frozen and sectioned into 7-mm thick slices using a microtome-cryostat. The tissue slices were collected on aminopropyl triethoxysilane-coated slides. The slides were washed with PBS (pH 7.4) to completely remove OCT and incubated overnight at 4° C. with an anti-*Salmonella* LPS antibody (1:100, Abcam #ab8274). Thereafter, Alexa Fluor 568-conjugated goat anti-mouse (1:100, Life Technologies A11031) antibody and Alexa Fluor 488-conjugated Phallodin (1:1000, Invitrogen #W21404) were used as secondary antibodies to detect F-actin. After the nuclei were stained with DAPI/Antifade (1:200, Invitrogen), the samples were mounted. Stained images were captured using Zeiss confocal microscope LSM 510 (Zeiss Laboratories), and representative images are given unless otherwise stated.

1-11. Statistical Analysis

Statistical analyses were performed using SPSS 18.0 statistical package (SPSS Inc., Chicago, IL, USA). Statistical significance of tumor growth between control and test groups was determined using two-tailed Student's t-test. P values <0.05 were considered statistically significant, and all data are expressed as mean±SD.

Example 2. Assay for In Vivo Toxicity of *Salmonella gallinarum* Strains and for Plasmid Stability 2-1. Assay for In Vitro Toxicity of *Salmonella gallinarum* Strains In order to apply *Salmonella gallinarum* strains to bacterial cancer therapy, wild-type *Salmonella gallinarum* was injected intravenously (i.v.) into the mice which were then analyzed for survival.

As a result, even though causing typhoid only in fowls, the intravenous injection of the wild-type *Salmonella gallinarum* strain (SG4021) induced death of all mice at a dose of about $10^5$ CFU or greater (FIG. 1A).

2-2. Determination of Dosage According to In Vivo Toxicity of Attenuated *Salmonella gallinarum* Strain Since the wild-type *Salmonella gallinarum* strain was observed to exhibit in vivo toxicity in Example 2-1, *Salmonella gallinarum* strain was attenuated by blocking the synthesis of ppGpp.

Briefly, the ppGpp-deleted (ΔppGpp) mutant *Salmonella gallinarum* strains of Example 1-2 in which both ppGpp synthetase I and II respectively encoded by relA and spoT genes had been mutated, and the *Salmonella typhimurium* were intravenously injected to BALB/c mice which were then analyzed for survival rate.

Figure 1B:
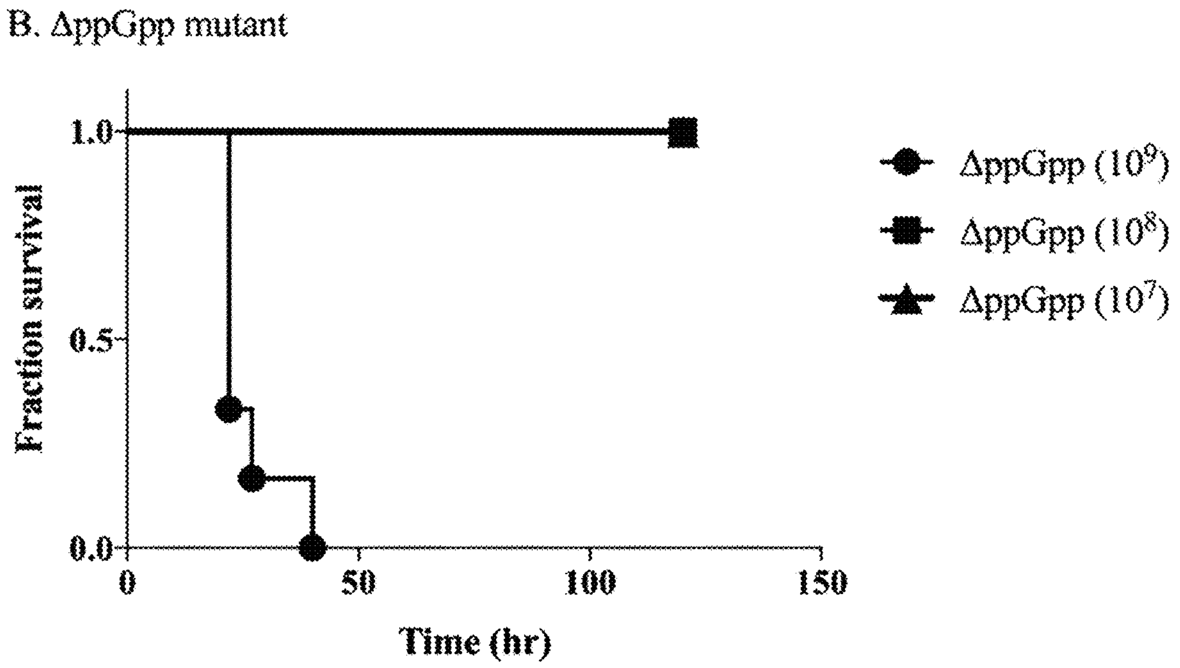

As a result, the mice were observed to survive up to $10^8$ CFU of the ΔppGpp *Salmonella gallinarum* strain (SG4023) (FIG. 1B) and up to about $10^7$ CFU of the ΔppGpp *Salmonella typhimurium* strain. Meanwhile, similar experiments were carried out with *Salmonella typhimurium* A1-R that can selectively infect and attack living tumors. As a result, it was observed that strains with modified lipopolysaccharide, msbB-mutation, (VN20009), and ΔrfaG/ΔrfaD double mutation were less prone to induce an immune response in the range of about $10^6$ to about $10^7$ CFU. Mice with tumors were observed to survive the intravenous infection of about $10^8$ CFU of *E. coli.*

It was understood from the data that with the assumption that *E. coli* was almost free of toxicity, the maximal dose of *Salmonella* spp. that animals free of nonspecific catastrophe can endure was about $10^8$ CFU.

2-3. Assay for Plasmid Stability

Figure 2:
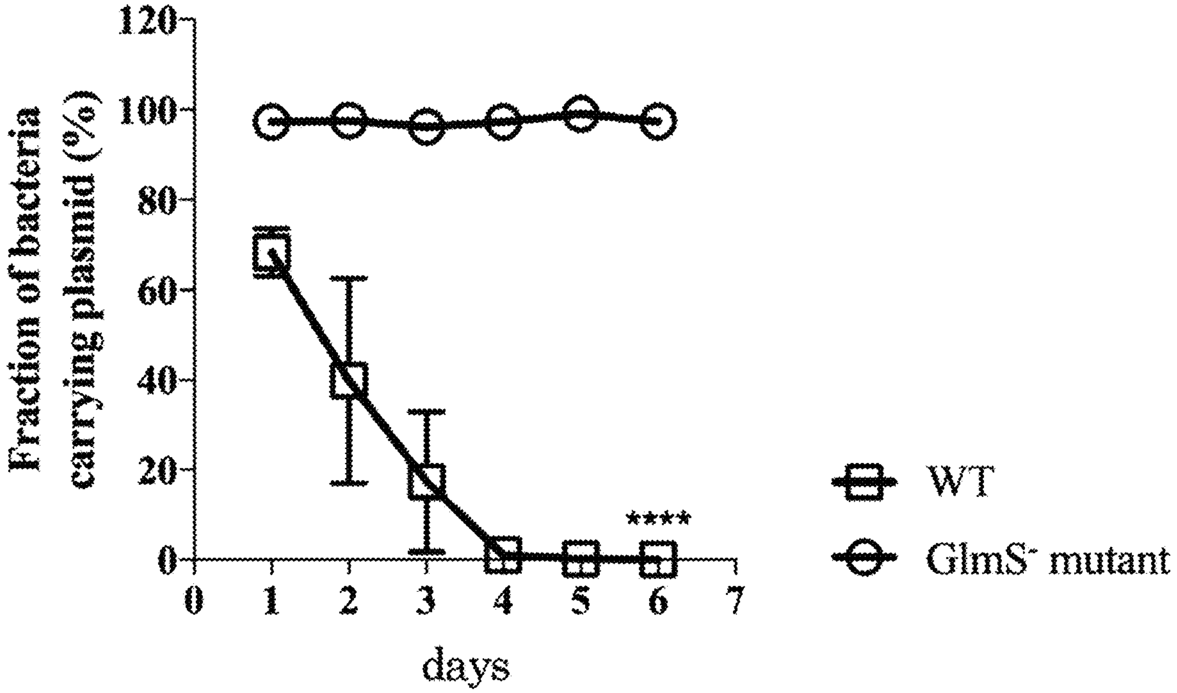
FIG. 2 shows plots illustrating comparison of plasmid stability between the *Salmonella* strain (SG4033) and lacking glmS and ppGpp genes that was transformed with the GlmS+pLux plasmid and the *Salmonella gallinarum* strain (SG4032) lacking ppGpp that was transformed with the GlmS+pLux plasmid.

With respect to the stability of the transformed plasmids, the same procedure as in Example 1-5 was carried out to evaluate whether the plasmids were lost. As a result, 99% of the plasmids carried by the wild-type *Salmonella gallinarum* strain (SG4021) were lost by day 4 while the plasmids carried by the glmS-deleted *Salmonella gallinarum* strain (SG4031) were completely maintained (FIG. 2).

Subsequent experiments employed the ΔppGpp strain, transformed with GlmS+pLux of Example 1-3, having a mutant glmS gene on the genome thereof so as to visualize *Salmonella gallinarum* strains in mice.

Example 3. Assay for Tumor Targeting of ΔppGpp *Salmonella gallinarum* Strain 3-1. Examination of Tumor Targeting According to Bioluminescence Signal Imaging To examine the tumor targeting of the ΔppGpp *Salmonella gallinarum* strain, bioluminescence signals of the *Salmonella gallinarum* strain were imaged in the same manner as in Example 1-9.

Figure 3:
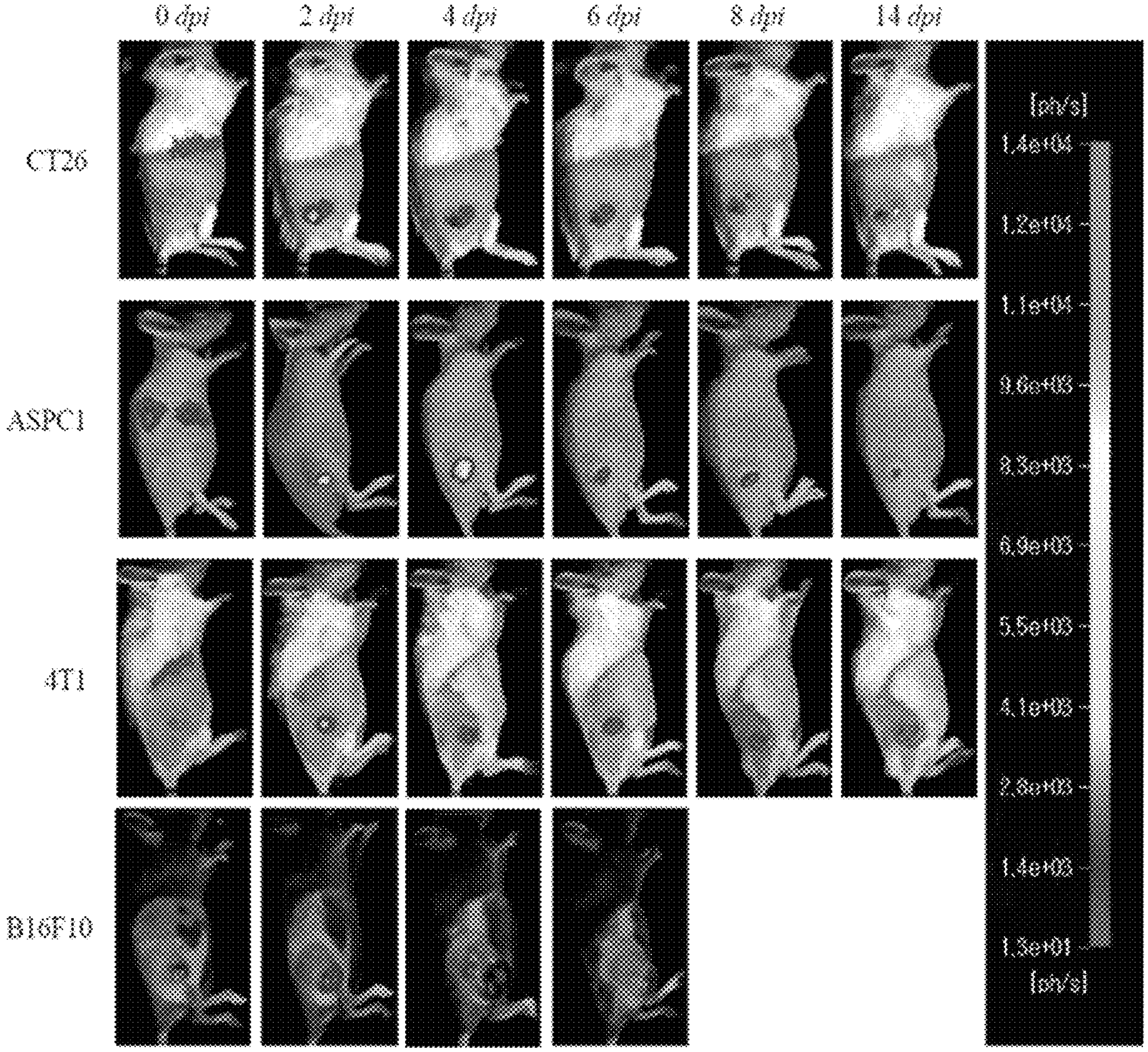
FIG. 3 shows images obtained through bioluminescence signal imaging device for results of targeting various tumors after intravenous injection of the *Salmonella gallinarum* strain (SG4033, ca. $1\times10^8$ CFU) transformed with the GlmS+pLux plasmid.
Figure 4:
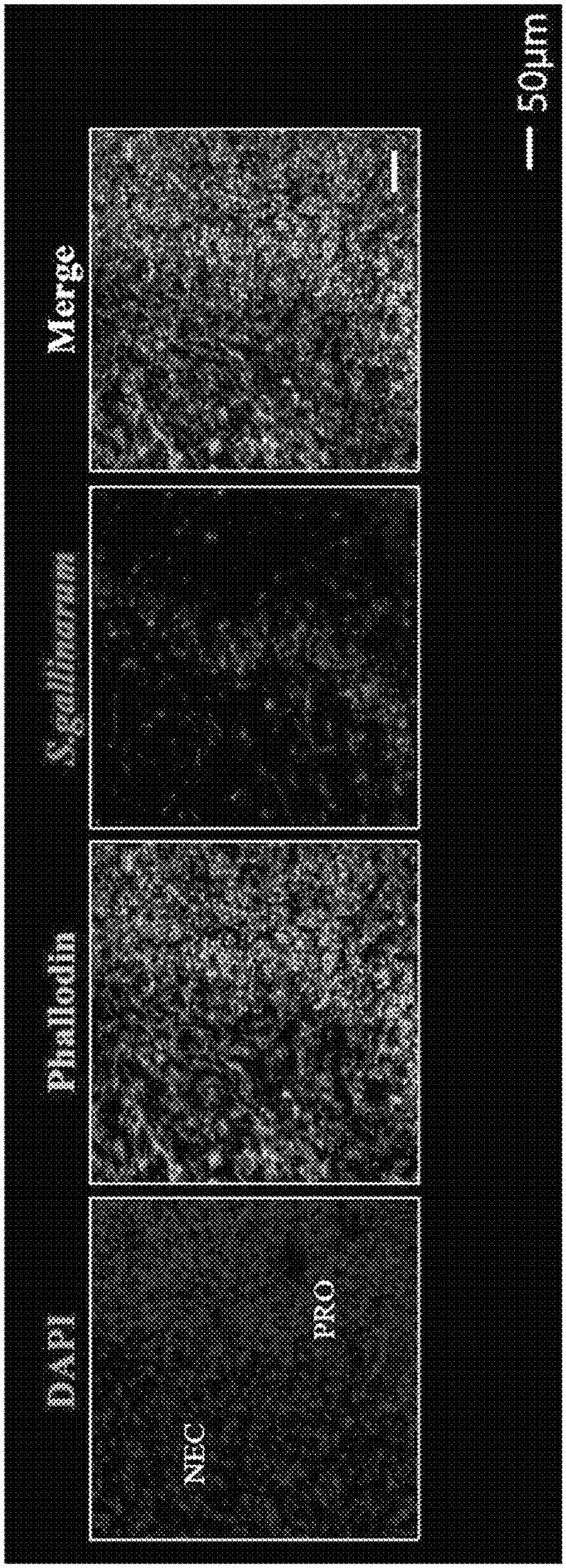
FIG. 4 shows images of CT26 tumor tissues stained with DAPI (nucleus), alexa Fluor 488-conjugated Phalloidin (actin), and a *Salmonella gallinarum*-specific antibody three days after injection of the ppGpp-deleted *Salmonella gallinarum* strain (SG4023, ca. $1\times10^8$ CFU).

As a result, bioluminescence signals were detected mainly from internal organs (liver and spleen) immediately after injection of the ΔppGpp *Salmonella gallinarum* strain (SG4031) (20 min, 0 day post injection (dpi)). Bioluminescence signals appeared only in the implanted tumor tissues. After appearance of peaks for AsPC-1 at 4 dpi and other tumors at 2 dpi, the bioluminescence signals were gradually diminished. Particularly, the *Salmonella gallinarum* strain was observed to target all the tumors implanted in three different mouse lines (FIG. 3). The presence of the ΔppGpp *Salmonella gallinarum* strain in implanted tumor tissues was confirmed at 3 dpi by staining the *Salmonella* strain in the implanted CT26 cells, with the detection of the *Salmonella* strain at the interface between a proliferative region and a necrotic region (FIG. 4).

3-2. Retention of Plasmid in Mouse

The wild-type and the mutant ΔppGpp *Salmonella gallinarum* strain of Example 1-2 including the GlmS+pLux carrying the mutant glmS gene of Example 1-3 were injected into Balb/c mice including CT26 cells and then imaged at 0, 2, and 4 dpi according to the method of Example 1-9.

Figure 5:
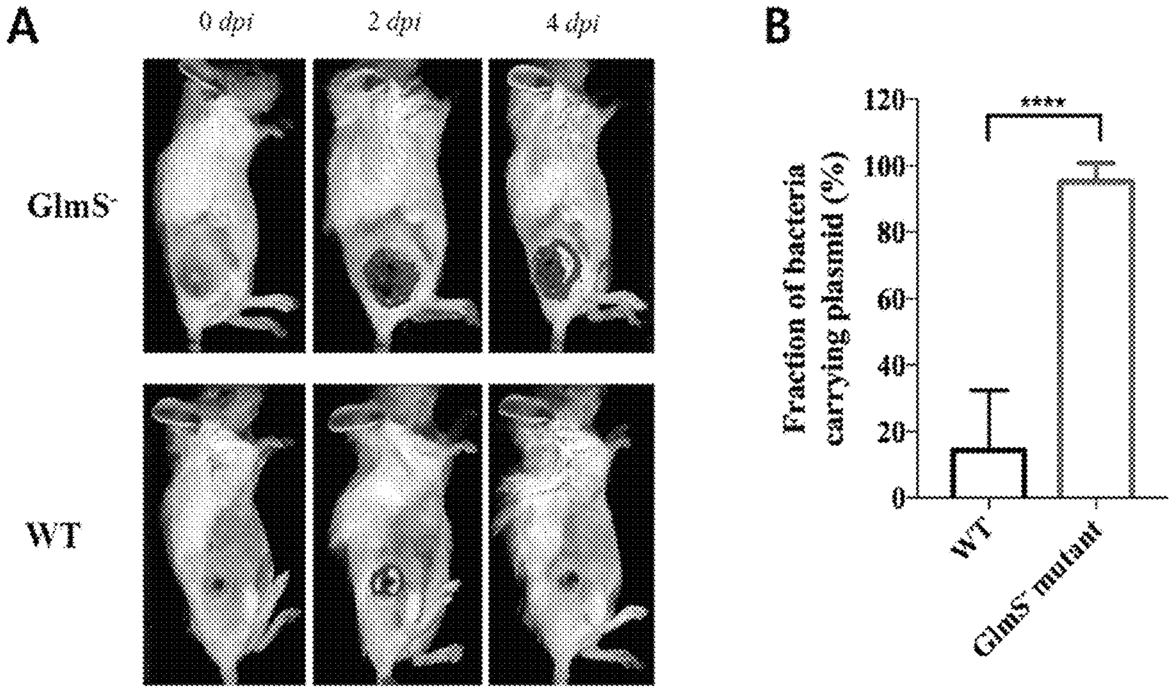
FIG. 5 shows (A) images of bioluminescence signals expressed with time from the GlmS+pLux plasmid transformed into the ppGpp-deleted *Salmonella gallinarum* strain (SG4032) including the wild-type glmS and the ppGpp-deleted *Salmonella gallinarum* strain (SG4033) lacking glmS, which targeted CT26 tumor tissues after intravenous injection (ca. 1×108 CFU) and (B) a graph of fractions of *Salmonella* strains including the GlmS+pLux plasmid seven days after injection of the *Salmonella* strains.

As a result, a strong bioluminescence signal was retained in the glmS-deleted ΔppGpp *Salmonella gallinarum* strain (SG4031), but not in the ΔppGpp *Salmonella gallinarum* strain (SG4023) (FIG. 5A). In addition, when the tumor-related *Salmonella gallinarum* strains were calculated at 7 dpi on ampicillin-containing plates, more than 90% of the wild type was found to lose the plasmids (FIG. 5B), demonstrating the excellency of the balanced-lethal host-vector system.

Example 4. Anticancer Effect of ΔppGpp *Salmonella Gallinarum* Strain on CT26 Tumor Mouse Model 4-1. Prolonged Duration of Life of *Salmonella gallinarum*-Treated Mouse To CT26 cell-implanted BALB/c mice, ΔppGpp *Salmonella gallinarum* was intravenously injected at a dose of about $1\times10^8$ CFU while the ΔppGpp *Salmonella typhimurium* was used as a control (ca. $1\times10^7$ CFU). In vivo anticancer activity of the ΔppGpp *Salmonella gallinarum* strains was analyzed according to Examples 1-8 and 1-10.

Figure 6:
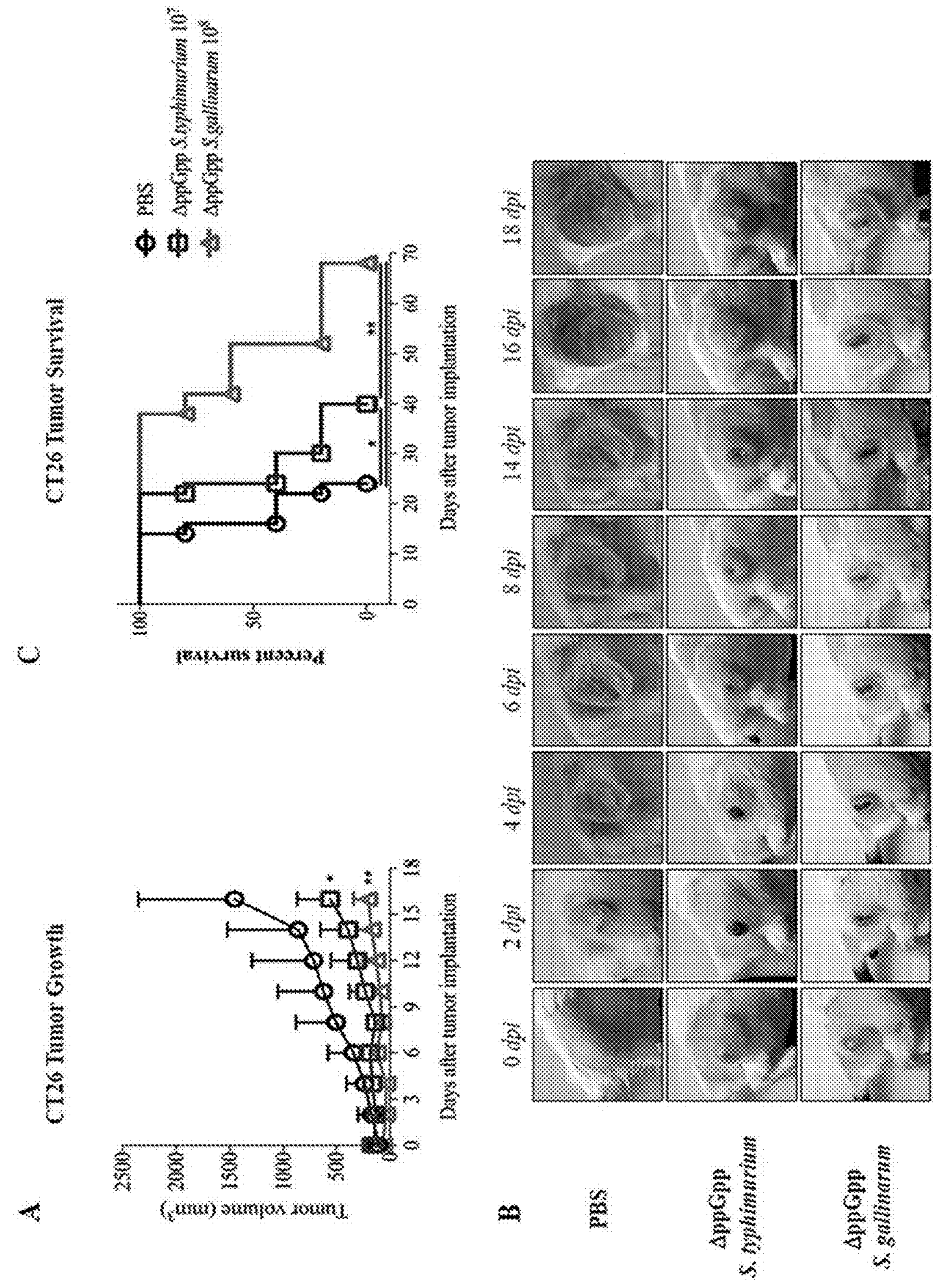
FIG. 6 shows (A) a plot of tumor volumes with time in CT26 cell-implanted BALB/c mice to which ca. $1\times10^8$ CFU of the ΔppGpp *Salmonella gallinarum* (SG4023) or ca. $1\times10^7$ CFU of the *Salmonella typhimurium* strain (SMR2130) was intravenously injected, (B) images illustrating changes of the implant tumors, and (C) a plot of survival rates of the mice.

Treatment of about $1\times10^8$ CFU of the ΔppGpp *Salmonella gallinarum* strain (SG4023) was observed to significantly improve the inhibitory effect of tumor growth in the mice, compared to the PBS control and about $1\times10^7$ CFU of the *Salmonella typhimurium* strain (SMR2130) (FIGS. 6A and 6B). That is, the group treated with the ΔppGpp *Salmonella gallinarum* group exhibited a prolonged duration of life, compared to the group treated with the ΔppGpp *Salmonella typhimurium* strain or PBS (FIG. 6C). The mice treated with about $1\times10^7$ CFU of the *Salmonella typhimurium* strain exhibited an average duration of life of about 24 days while the mice treated with about $1\times10^8$ CFU of *Salmonella gallinarum* survived for 53 days on average. Furthermore, the duration of life of the mice treated with $1\times10^8$ CFU of the *Salmonella gallinarum* remarkably increased (3.5 folds), compared to the PBS control (15 days).

4-2. Distribution Pattern of *Salmonella gallinarum* Strain in Mouse

To examine distribution patterns of *Salmonella gallinarum* strains in mice, temporal changes in the number of the *Salmonella gallinarum* strains were monitored in mouse organs.

Figure 7A:
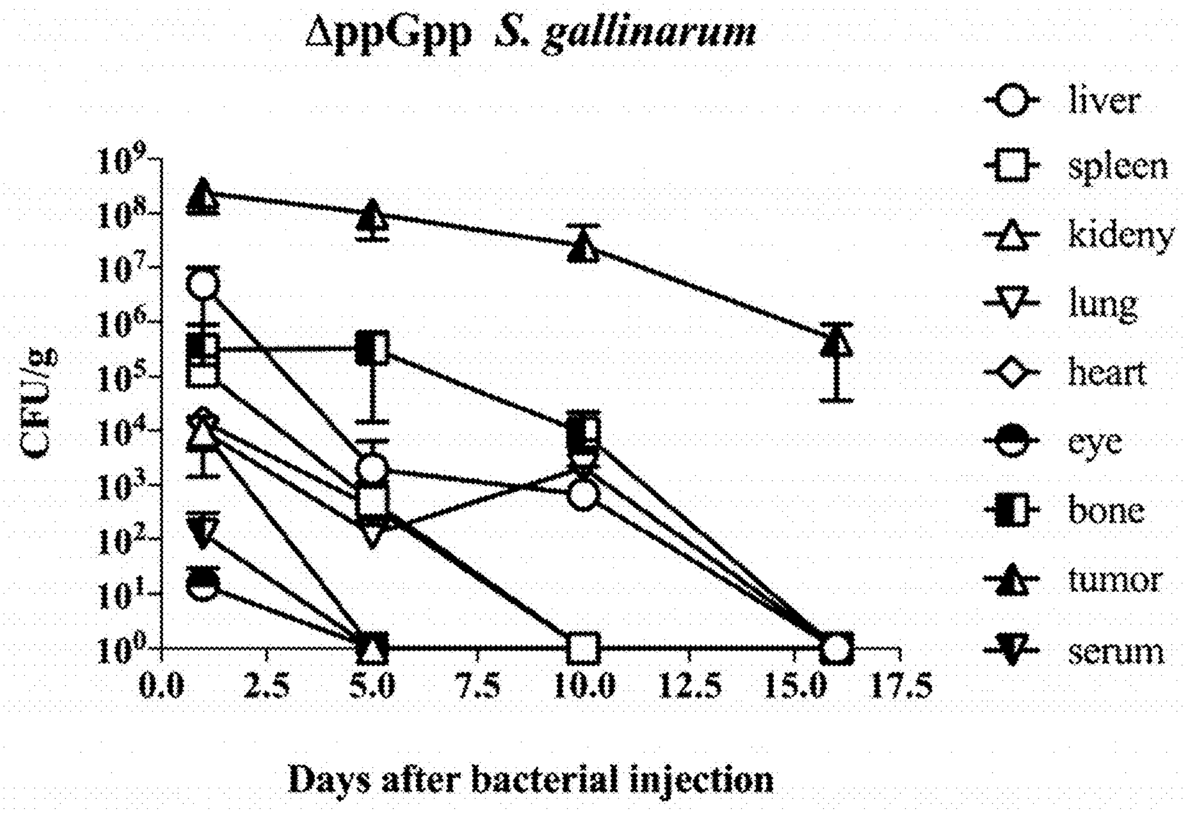
FIG. 7 shows plots of numbers of *Salmonella* strains with time in various organs of CT26 cell-implanted BALB/c mice to which (A) ca. $1\times10^8$ CFU of the ΔppGpp *Salmonella gallinarum* strain (SG4022) and (B) ca. $1\times10^7$ CFU of the ΔppGpp *Salmonella typhimurium* (SHJ2037) were intravenously injected.
Figure 7B:
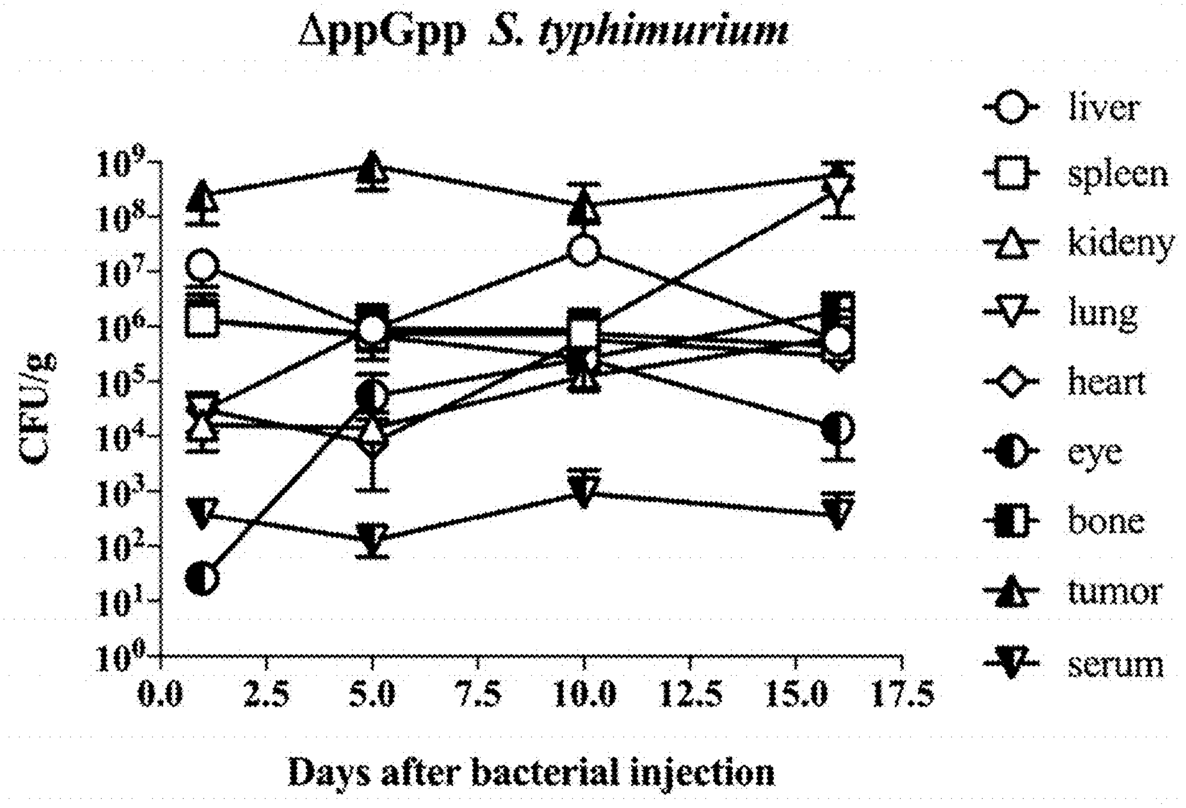

As a result, maximal highest levels ($10^8$ to $10^9$ CFU/g) in tumors were observed in both of the *Salmonella* strains one day after the injection (1 dpi). The ΔppGpp *Salmonella typhimurium* strain (SHJ2037) was maintained at the same level in tumor while the number of the ΔppGpp *Salmonella gallinarum* strain (SG4022) was gradually reduced into $10^6$ CFU/g over 16 days. At 1 dpi, the *Salmonella typhimurium* strain was maintained at a level of $10^6$ to $10^7$ CFU/g in liver, spleen, and bone, at a level of $10^6$ to $10^7$ CFU/g, at a level of $10^4$ CFU/g in lung, kidney, and heart, and at a level of $10^1$ and $10^3$ CFU/g in serum and eye, and the levels were not significantly reduced over 16 days. In contrast, the *Salmonella gallinarum* strain was found to exhibit similar distribution patterns for the organs at 1 dpi. The *Salmonella gallinarum* strain was completely cleared from the organs by 16 dpi (FIG. 7).

From the data obtained above, it is understood that the ΔppGpp *Salmonella gallinarum* strain possessing the mutant glmS gene on the chromosome thereof specifically targets tumors to exhibit an anti-tumor effect and as such, can be used for anti-tumor purposes.

The disclosure has been described above with reference to the preferred embodiments. It will be understood by those skilled in the art that the disclosure may be embodied in various other forms without departing from the spirit or essential characteristics thereof. Therefore, the above-described embodiments should be considered in an illustrative rather than a restrictive sense. The scope of the disclosure is defined by the appended claims rather than by the foregoing description, and all differences within the scope of equivalents thereof should be construed as being included in the disclosure.

The invention claimed is:

1. A method for treatment of a tumor in a subject, the method comprising administering to the subject a composition comprising an attenuated *Salmonella gallinarum* strain lacking guanosine tetraphosphate (ppGpp) production capability, wherein the strain lacks a glmS gene.

2. The method of claim 1, wherein the tumor is a solid cancer.

3. The method of claim 1, wherein the tumor is adenocarcinoma.

4. The method of claim 1, wherein the tumor is a cancer selected from the group consisting of colorectal cancer, pancreatic cancer, skin cancer, and breast cancer.

* * * * *